United States Patent [19]

King et al.

[11] Patent Number: 5,210,322

[45] Date of Patent: *May 11, 1993

[54] PROCESSES FOR THE PREPARATION OF ETHERS

[75] Inventors: Stephen W. King, Scott Depot; Kurt D. Olson, Cross Lanes, both of W. Va.

[73] Assignee: Union Carbide Chemicals & Plastics Technology Corporation, Danbury, Conn.

[*] Notice: The portion of the term of this patent subsequent to Mar. 2, 2010 has been disclaimed.

[21] Appl. No.: 585,455

[22] Filed: Sep. 20, 1990

[51] Int. Cl.$^5$ .................... C07C 41/00; C07C 69/96
[52] U.S. Cl. .................... 568/579; 568/613; 568/618; 568/619; 568/625; 568/671; 568/699; 568/606; 568/607; 568/608; 568/609; 568/610; 568/614; 568/620; 568/621; 568/622; 568/623; 568/624; 568/659; 568/660; 568/661; 568/662; 568/663; 568/664; 568/670; 568/67; 568/675; 568/676; 568/678; 568/679; 568/680; 560/179; 560/186; 562/423; 558/275; 558/277
[58] Field of Search .............. 568/579, 678, 613, 618, 568/619, 608, 609, 610, 614, 607, 620, 621, 622, 623, 624, 659, 660, 661, 662, 683, 664, 670, 673, 675, 676; 558/275, 277

[56] References Cited

U.S. PATENT DOCUMENTS 4,308,402 12/1981 Edwards et al. .................... 568/618

OTHER PUBLICATIONS

March, J., Advanced Organic Chemistry: Reactions, Mechanisms, and Structure, 1968, pp. 435-436, 477-480, 878-879 and 316.
Tamura, Y. et al., Synthesis, 1975, pp. 641-642.
Taylor, Roger, Tetrahedron Letters, No. 8, 1975, pp. 593-596.
Witt, H. et al., Angew Chem., 1970, 82, p. 79.
Tundo, Pietro et al., Ind. Eng. Chem. Res., 1988, 27, pp. 1565-1571.
Dow Chemical U.S.A., Experimental Ethylene Carbonate XAS-1666.00L Product Bulletin (1982), p. 12.
Texaco Chemical Company, TEXACAR ® Ethylene and Propylene Carbonates Product Bulletin (1987), p. 24.

Primary Examiner—Paul J. Killos
Attorney, Agent, or Firm—R. M. Allen

[57] ABSTRACT

A process for preparing ethers which comprises contacting a carboxylated ether with a metal oxide catalyst under conditions effective to produce the ether.

65 Claims, No Drawings

PROCESSES FOR THE PREPARATION OF ETHERS

RELATED APPLICATIONS

The following are related, commonly assigned applications, filed on an even date herewith:

U.S. patent application Ser. No. 07/585,561; U.S. patent application Ser. No. 07/585,560; U.S. patent application Ser. No. abandoned 07/585,563; U.S. patent application Ser. No. 07/585,564; U.S. patent application Ser. No. abandoned 07/585,559; U.S. patent application Ser. No. 07/585,456; U.S. patent application Ser. No. 07/585,565; U.S. patent application Ser. No. 07/585,555; and U.S. patent application Ser. No. (U.S. Pat. No. 5,104,987) 07/585,556; all of which are incorporated herein by (U.S. Pat. No. 5,164,497) reference.

BRIEF SUMMARY OF THE INVENTION

1. Technical Field

This invention relates to a process for preparing ethers which comprises contacting a carboxylated ether with a metal oxide catalyst under conditions effective to produce the ether.

2. Background of the Invention

Decarboxylation, that is, elimination of the —COOH group as $CO_2$, is a known process. March, J., Advanced Organic Chemistry: Reactions, Mechanisms, and Structure, 1968, pp. 435-436, 477-480 and 878-879, describes various decarboxylation reactions. At pages 435-436, it is stated that aromatic acids can be decarboxylated by heating with copper and quinoline. At pages 477-480, it is stated that aliphatic acids which undergo successful decarboxylation have certain functional groups or double or triple bonds in the alpha or beta positions such as malonic acids, alpha-cyano acids, alpha-nitro acids, alpha-aryl acids, alpha-keto acids, alpha-trihalo acids, beta-keto acids, beta,gamma-olefinic acids and the like. At pages 878-879, oxidative decarboxylation is described in which lead tetraacetate cleaves carboxyl groups, replacing them with acetoxy groups, which may be hydrolyzed to hydroxyl groups. It is stated that compounds containing carboxyl groups on adjacent carbons (succinic acid derivatives) can be bisdecarboxylated with lead tetraacetate. It is also stated that compounds containing geminal carboxyl groups (malonic acid derivatives) can be bisdecarboxylated with lead tetraacetate, gem-diacetates (acylals) being produced, which are hydrolyzable to ketones.

Various processes for the production of ethers are known. A method commonly employed for the preparation of ethers is known as the Williamson synthesis. In the Williamson synthesis, an alkyl halide or substituted alkyl halide is reacted with a sodium alkoxide or sodium phenoxide to give the ether product. For the preparation of aryl methyl ethers, methyl sulfate is frequently used instead of methyl halides. The Williamson synthesis involves nucleophilic substitution of an alkoxide ion or phenoxide ion for a halide ion. Aryl halides cannot in general be used because of their low reactivity toward nucleophilic substitution. Disadvantages associated with the Williamson synthesis include the production of a mole of by-product salt for each mole of ether product and the use of certain methylating agents such as methyl chloride and methyl sulfate which have toxicity and handling problems. Also, at page 316 of March, J., supra, it is stated that the Williamson reaction, i.e., $RX + OR'^{31} \rightarrow ROR'$, is not successful for tertiary R (because of elimination) and low yields are obtained with secondary R.

Other processes have been developed for the production of ethers. U.S. Pat. No. 4,308,402 discloses a process for cleaving a terminal —$CH_2OH$ moiety from an alkoxyalkanol by reacting an alkoxyalkanol at elevated temperatures in the presence of heterogeneous nickel. The process is believed to involve an initial dehydrogenation of an alcohol to afford an aldehyde followed by decarbonylation to afford a methylated ether compound.

Tamura, Y. et al., Synthesis, 1975, 641-642, relates to the preparation of unsymmetrical sulfides by the alkylation of thiols with alkyl carbonates in the presence of sodium ethoxide and ethanol under refluxing conditions.

Enichem Synthesis SpA, Dimethyl Carbonate Product Bulletin, p. 10, discloses the reaction of phenols with dimethyl carbonate in the presence of a basic catalyst such as NaOH, $Na_2CO_3$, $NaOCH_3$, tertiary amines or heterocyclic nitrogenous compounds to give methylated phenols. Reaction temperatures of at least 140° C. are required. It is stated that the speed of reaction can be accelerated with catalytic quantities of organic and inorganic halides.

Taylor, Roger, Tetrahedron Letters, No. 8, 1975, 593-596, discloses the thermal decomposition of carbonates to ethers utilizing a palladium-charcoal catalyst.

Witt, H. et al., Angew. Chem., 1970, 82, 79, describes the preparation of substituted diphenyl ethers from ortho- and para-substituted diphenyl carbonates in the presence of small amounts of potassium carbonate and at a temperature of 180° C.-260° C.

Tundo, Pietro et al., Ind. Eng. Chem. Res., 1988, 27, 1565-1571, describes the reaction of dialkyl carbonates with phenols, thiophenols and mercaptans under gas-liquid phase-transfer conditions (continuous flow of gaseous reactants over a solid bed supporting a liquid phase-transfer catalyst) to produce the corresponding ethers and thioethers. The solid bed consisted of potassium carbonate coated with 5 weight percent of CARBOWAX ® poly(oxyethylene)glycol 6000 for one set of experiments and alpha-alumina pellets coated with 5 weight percent of potassium carbonate and 5 weight percent of CARBOWAX ® poly(oxyethylene)glycol 6000 for another set of experiments. Tundo et al. state at page 1568, right hand column, lines 33-42, that the reaction of alcohols with dialkyl carbonates produces only transesterification.

Dow Chemical U.S.A., Experimental Ethylene Carbonate XAS -1666.00L Product Bulletin (1982), p. 12, describes the preparation of ethylene sulfide from the reaction of ethylene carbonate with potassium thiocyanate at a temperature of 100° C. It is stated that 2-oxazolidinones can be prepared from the reaction of aryl or alkyl isocyanates with ethylene carbonate in the presence of a catalyst. It is also stated that ethylene carbonate slowly decomposes to ethylene oxide in quantitative yields at a temperature above 200° C. and that this reaction is accelerated by the presence of catalysts such as inorganic and organic salts.

Texaco Chemical Company, TEXACAR ® Ethylene and Propylene Carbonates Product Bulletin (1987), p. 24, discloses the reaction of ethylene carbonate with glycerine to give glycidol. It is stated that this reaction probably proceeds through the cyclic carbonate ester of glycerine. It is also stated that ethylene carbonate may be reacted with potassium thiocyanate at elevated temperature to give ethylene sulfide.

DISCLOSURE OF THE INVENTION

This invention relates to a process for preparing ethers which comprises contacting a carboxylated ether with a metal oxide catalyst under conditions effective to produce the ether.

This invention also relates to a process for preparing ethers which comprises contacting an active hydrogen-containing compound with a $CO_2$ synthon in the presence of a metal oxide catalyst under conditions effective to produce the ether.

This invention further relates to a process for preparing ethers which comprises (i) contacting an active hydrogen-containing compound with a $CO_2$ synthon under conditions effective to produce a carboxylated ether, and (ii) contacting the carboxylated ether with a metal oxide catalyst under conditions effective to produce the ether.

In a preferred embodiment, the processes of this invention can provide ether compounds such as ethylene glycol dimethyl ethers resulting from the reaction of poly(oxyethylene)glycols and dimethyl carbonate with no by-product salt formation. As indicated above, a disadvantage associated with conventional Williamson ether synthesis is by-product salt formation.

In another preferred embodiment of this invention, high yields of ether compounds can be obtained utilizing secondary alcohols as starting materials. As indicated above, a disadvantage associated with conventional Williamson ether synthesis is the low yields of ether product obtained with secondary alcohol starting materials.

End-capping of active hydrogen-containing compounds is a further preferred embodiment of this invention. Suitable active hydrogen-containing compounds such as alcohols, glycols, poly(oxyalkylene)glycols such as CARBOWAX ® poly(oxyethylene)glycols and POLYOX ® poly(oxyethylene)glycols, surfactants such as TERGITOL ® nonionic surfactants and other ethylene oxide and/or propylene oxide derivatives, e.g., UCON ® fluids and lubricants can be reacted with a suitable $CO_2$ synthon such as dimethyl carbonate or diethyl carbonate in the presence of a metal oxide catalyst under conditions effective to end-cap the active hydrogen-containing compound. Methyl-capping and ethyl-capping preferably afford desired ether products, e.g., SELEXOL ® materials, such as ethylene glycol dimethyl ethers and ethylene glycol diethyl ethers, e.g., monoethylene glycol dimethyl or diethyl ether, diethylene glycol dimethyl or diethyl ether, triethylene glycol dimethyl or diethyl ether, tetraethylene glycol dimethyl or diethyl ether and polyethylene glycol dimethyl or diethyl ethers.

The ethers produced in accordance with the processes of this invention are useful for a wide variety of applications such as solvents, liquid absorbents, complexing agents, phase transfer catalysts, PCB destruction, electronics, absorption refrigeration, recovery of metals, acid extraction, gas absorption, polymerization catalysts, polymer modification, photography, printing, pharmaceutical formulations, fuel additives, fragrances, flavors and the like.

For purposes of this invention, the chemical elements are identified in accordance with the Periodic Table of the Elements, CAS version, Handbook of Chemistry and Physics, 67th Ed., 1986–87, inside cover. Also, for purposes of this invention, Group IIIB metal oxides embraces the lanthanides and actinides. As used herein, the term "oxide" embraces oxides, hydroxides and/or mixtures thereof. Also, as used herein, the term "$CO_2$ synthon" embraces $SO_2$ synthons such as sulfurous acids and sulfurous acid esters. Sulfur analogs of ethers, i.e., thioethers, are also embraced by this invention.

DETAILED DESCRIPTION

As indicated above, this invention relates to a process for preparing ethers which comprises contacting a carboxylated ether with a metal oxide catalyst under conditions effective to produce the ether.

As also indicated above, this invention relates to a process for preparing ethers which comprises contacting an active hydrogen-containing compound with a $CO_2$ synthon in the presence of metal oxide catalyst under conditions effective to produce the ether.

As further indicated above, this invention relates to a process for preparing ethers which comprises (i) contacting an active hydrogen-containing compound with a $CO_2$ synthon under conditions effective to produce a carboxylated ether, and (ii) contacting the carboxylated ether with a metal oxide catalyst under conditions effective to produce the ether.

When an active hydrogen-containing compound and $CO_2$ synthon are employed as starting materials, it is believed that a transesterification reaction followed by a decarboxylation reaction occurs to provide the desired ether product. The exact reaction mechanism is not fully appreciated but what is appreciated is that an active hydrogen-containing compound starting material and $CO_2$ synthon starting material can be contacted in the presence of a metal oxide catalyst under conditions described herein to provide an ether product. It is also appreciated that a carboxylated ether can be contacted with a metal oxide catalyst under conditions described herein to provide an ether product.

Step (i) of certain processes of this invention can in general be referred to as a transesterification reaction. Any suitable transesterification catalyst can be employed in step (i). Such transesterification catalysts are known and include, for example, basic metal oxides, alkoxides and other basic metal salts such as potassium carbonate, sodium titanate and the like. Other suitable transesterification catalysts include, for example, Bronsted acids such as sulfuric acid and Lewis acids such as aluminum triisopropoxide. As discussed hereinafter in regard to the decarboxylation catalyst, the transesterification catalyst employed in this invention likewise may also contain support(s), binding agent(s) or other additives to stabilize or otherwise help in the manufacture of the catalyst. Both homogeneous and heterogeneous catalysts can be employed in the step (i) reaction. The amount of transesterification catalyst used in step (i) is dependent on the particular catalyst employed and can range from about 0.01 weight percent or less to about 10 weight percent or greater of the total weight of the starting materials.

Suitable active hydrogen-containing compound starting materials which can be employed in the step (i) transesterification reaction include any permissible substituted or unsubstituted active hydrogen-containing organic compound(s). Illustrative active hydrogen-containing compound starting materials useful in this invention include, for example, substituted and unsubstituted alcohols, phenols, carboxylic acids, amines and the like. Preferred active hydrogen-containing compounds include alcohols and phenols. The molar ratio of active hydrogen-containing compound to $CO_2$ synthon is not narrowly critical and can range from about 0.05:1 or less to about 50:1 or greater, preferably from about 0.1:1 to about 10:1.

Suitable active hydrogen-containing compounds include substituted and unsubstituted alcohols (mono-, di- and polyhydric alcohols), phenols, carboxylic acids (mono-, di- and polyacids), and amines (primary and secondary). Other suitable active hydrogen-containing compounds include substituted and unsubstituted thiophenols, mercaptans, amides and the like. Frequently, the organic compounds contain 1 carbon to about 100 or 150 carbons (in the case of polyol polymers) and can contain aliphatic and/or aromatic structures. Most often, the organic compounds are selected from the group of mono-, di- and trihydric alcohols having 1 to about 30 carbon atoms. The organic compounds having active hydrogens can be the product of hydroformylation/hydrogenation reactions.

Suitable alcohols include primary and secondary monohydric alcohols which are straight or branched chain such as methanol, ethanol, propanol, pentanol, hexanol, heptanol, octanol, nonanol, decanol, undecanol, dodecanol, tridecanol, tetradecanol, pentadecanol, hexadecanol, octadecanol, isopropyl alcohol, 2-ethylhexanol, sec-butanol, isobutanol, 2-pentanol, 3-pentanol and isodecanol. Particularly suitable alcohols are linear and branched primary alcohols (including mixtures) such as produced by the "Oxo" reaction of $C_3$ to $C_{20}$ olefins. The alcohols may also be cycloaliphatic such as cyclopentanol, cyclohexanol, cycloheptanol, cyclooctanol, as well as aromatic substituted aliphatic alcohols such as benzyl alcohol, phenylethyl alcohol, and phenylpropyl alcohol. Other aliphatic structures include 2-methoxyethanol and the like.

Phenols include alkylphenols of up to 30 carbons such as p-methylphenol, p-ethylphenol, p-butylphenol, p-heptylphenol, p-nonylphenol, dinonylphenol and p-decylphenol. The aromatic radicals may contain other substituents such as halide atoms.

Alcohols (polyols) having 2 or more hydroxyl groups, e.g., about two to six hydroxyl groups and have 2 to 30 carbons, include glycols such as ethylene glycol, propylene glycol, butylene glycol, pentylene glycol, hexylene glycol, neopentylene glycol, decylene glycol, diethylene glycol, triethylene glycol and dipropylene glycol. Other polyols include glycerine, 1,3-propanediol, pentaerythritol, galactitol, sorbitol, mannitol, erythritol, trimethylolethane and trimethylolpropane.

Carboxylic acids include formic acid, acetic acid, propionic acid, butyric acid, valeric acid, caproic acid, caprylic acid, capric acid, lauric acid, myristic acid, palmitic acid, stearic acid, oleic acid, linoleic acid and linolenic acid. Other carboxylic acids include benzoic acid, cyclohexane carboxylic acid, phenylacetic acid, toluic acid, chlorobenzoic acid, bromobenzoic acid, nitrobenzoic acid, phthalic acid, isophthalic acid, terephthalic acid, salicylic acid, hydroxybenzoic acid, anthranilic acid, aminobenzoic acid, methoxybenzoic acid and the like.

Amines include methylamine, dimethylamine, ethylamine, diethylamine, n-propylamine, di-n-propylamine, isopropylamine, n-butylamine, isobutylamine, cyclohexylamine, piperazine, benzylamine, phenylethylamine, monoethanolamine, diethanolamine, aminoethylethanolamine, ethylenediamine, diethylenetriamine, triethylenetetramine, tetraethylenepentamine, pentaethylenehexamine, tetramethylenediamine and hexamethylenediamine. Other amines include aniline, methylaniline, toluidine, anisidine, chloroaniline, bromoaniline, nitroaniline, diphenylamines, phenylenediamine, benzidine, aminobenzoic acid, sulfanilic acid and sulfanilamide. Still other amines include acetanilide, benzanilide, aceto-toluidide, nitroacetanilide and the like.

Preferred active hydrogen-containing starting materials which can be employed in the step (i) transesterification reaction include hydroxyl-containing organic compounds such as those embraced by the formula $R(OH)_m$ wherein R is the residue of an organic compound and m is a value which satisfies the valencies of R, preferably m is a value of from 1 to about 6, more preferably m is a value of from 1 to about 4. Preferred hydroxyl-containing compound starting materials include monohydric, dihydric and polyhydric alcohols. Illustrative hydroxyl-containing compound starting materials useful in this invention include, for example, 2-(2-methoxyethoxy)ethanol, 2-(2-butoxyethoxy)ethanol, 2-methoxyethanol, alkoxy or allyloxy poly(oxyalkylene)glycols such as alkoxy or allyloxy CARBOWAX® poly(oxyethylene)glycol materials, ethylene glycol, diethylene glycol, triethylene glycol, tetraethylene glycol, pentaethylene glycol, hexaethylene glycol, poly(oxyalkylene)glycols such as CARBOWAX® poly(oxyethylene)glycols and POLYOX® poly(oxyethylene)glycols, poly(oxyethylene)(oxypropylene)glycols, phenol, allyl alcohol, diethanolamine, triethanolamine, monoethanolamine, surfactants such as TERGITOL® nonionic surfactant materials, alkoxy or allyloxy poly(oxyethylene)(oxypropylene)glycols such as UCON® lubricant and fluid materials, 1-methoxy-2-hydroxypropane, 2-propanol, cyclohexanol and the like.

Suitable $CO_2$ synthon starting materials which can be employed in the step (i) transesterification reaction include any permissible substituted or unsubstituted carboxyl-containing compound(s) or carbonyl-containing compound(s) which are capable of reacting with an active hydrogen-containing compound under the process conditions described herein, such as those embraced by the formulae $R_1C(O)R_2$ or $R_1S(O)R_2$ wherein $R_1$ is hydrogen, halogen, amino, hydroxyl or the residue of an organic compound, and $R_2$ is amino, hydroxyl or the residue of an organic compound. Illustrative $CO_2$ synthons include, for example, substituted and unsubstituted carbonates, chlorocarbonates, carbonic acids, carbamates, carbamic acids, oxalates, 2-oxazolidinones, ureas, esters, phosgene, chloroformates, carbon dioxide, orthocarboxylates, sulfurous acids, sulfurous acid esters and the like. For purposes of this invention, carbon monoxide is also considered a $CO_2$ synthon for appropriate oxidative carbonylation reactions. Preferred $CO_2$ synthons include, for example, diethyl carbonate, ethylene carbonate, dimethyl carbonate, 2-oxazolidinone, ethylene sulfite, phosgene and the like. The use of $CO_2$ synthons prepared in situ such as the reaction of ethylene carbonate and monoethanolamine to give 2-oxazolidinone is encompassed within the scope of this invention.

As indicated above, $R_1$ and $R_2$ can be the residue of an organic compound. Illustrative residues of organic compounds include, for example, alkyl, aryl, alkylamino, arylamino, cycloalkyl, heterocycloalkyl, alkyloxy, aryloxy, cycloalkyloxy, heterocycloalkyloxy, alkyloxycarbonyl, aryloxycarbonyl, cycloalkyloxycarbonyl, heterocycloalkyloxycarbonyl, hydroxycarbonyl and the like. Additionally, for purposes of defining the $CO_2$ synthon by the formulae above, the $R_1$ and $R_2$ substituents together can complete a cycloalkyl ring or a heterocycloalkyl ring which can be substituted or unsubstituted. The $R_1C(O)R_2$ formula is also contemplated to embrace carbon dioxide and carbon monoxide.

The step (i) transesterification reaction can be conducted over a wide range of pressures ranging from atmospheric or subatmospheric pressures to superatmospheric pressures. However, the use of very high pressures has not been observed to confer any significant advantages but increases equipment costs. Further, it is preferable to conduct the step (i) reaction at reduced pressures of from about 1 mm Hg to less than about 760 mm Hg. The step (i) transesterification reaction is preferably effected in the liquid or vapor states or mixtures thereof.

The temperature of the step (i) transesterification reaction may be as low as about ambient temperature to about 300° C. Preferably, the reaction temperature ranges from about 50° C. to about 200° C., and most preferably from about 60° C. to about 120° C.

Suitable carboxylated ethers prepared by the step (i) transesterification reaction include any permissible substituted or unsubstituted carboxyl-containing ether compounds which are capable of eliminating carbon dioxide under the Process conditions described herein, e.g., oxalates, carbonates, carbamates and the like, such as those embraced by the formulae $ROC(O)OR_1$, $ROC(O)OR_2$, $ROC(O)OC(O)OR_1$, $ROC(O)OC(O)OR_2$ and the like wherein R, $R_1$ and $R_2$ are as defined above. It is understood that the R and $R_1$ substituents together and the R and $R_2$ substituents together can complete a heterocycloalkyl ring which can be substituted or unsubstituted. Illustrative carboxylated ethers include, for example, monoethylene glycol dimethyl or diethyl or diallyl carbonate, diethylene glycol dimethyl or diethyl or diallyl carbonate, triethylene glycol dimethyl or diethyl or diallyl carbonate, tetraethylene glycol dimethyl or diethyl or diallyl carbonate, polyethylene glycol dimethyl or diethyl or diallyl carbonates, polyethylene glycol diisopropyl carbonates, bisglycidyl carbonate and the like. The amount of carboxylated ether(s) employed in step (ii) is dependent on the amount of metal oxide catalyst employed.

Illustrative preferred carboxylated ethers include, for example, bis[2-(2-methoxyethoxy)ethyl]-carbonate, bis(2-methoxyethyl)carbonate, bis[2-(2-butoxyethoxy)ethyl]carbonate, 2-methoxyethyl 2-(2-methoxyethoxy)ethyl carbonate, bis(triethylene glycol monomethyl)-carbonate, 2-(2-methoxyethoxy)ethyl triethylene glycol monomethyl carbonate, bis(tetraethylene glycol monomethyl)carbonate, triethylene glycol monomethyl tetraethylene glycol monomethyl carbonate, bis(2-butoxyethyl)carbonate and the like.

The carboxylated ethers prepared by the step (i) transesterification reaction may undergo one or more transesterifications prior to the step (ii) decarboxylation reaction. For example, an active hydrogen-containing compound different from the active hydrogen-containing compound starting material may be reacted with the originally prepared carboxylated ether under conditions effective to prepare a different carboxylated ether. Suitable active hydrogen-containing compounds include those embraced by the formula $R_3OH$ wherein $R_3$ is the residue of an organic compound. This invention is not intended to be limited in any manner by the step (i) transesterification reaction.

The carboxylated ethers and ethers prepared in accordance with this invention can be either symmetrical or unsymmetrical. For the preparation of carboxylated ethers and ethers having a symmetrical configuration, it is preferred to use an alkylene carbonate, e.g., ethylene carbonate or phosgene, as the $CO_2$ synthon starting material or a molar excess of any active hydrogen-containing compound starting material with any $CO_2$ synthon starting material, e.g., a molar ratio of active hydrogen-containing compound to $CO_2$ synthon of from about 3:1 to about 10:1. For the preparation of carboxylated ethers and ethers having an unsymmetrical configuration, it is preferred to use a $CO_2$ synthon starting material other than an alkylene carbonate, e.g., dimethyl carbonate, or an equimolar or molar excess of any $CO_2$ synthon starting material with any active hydrogen-containing compound starting material, e.g., a molar ratio of active hydrogen-containing compound to $CO_2$ synthon of from about 0.1:1 to about 1:1.

Step (ii) of certain processes of this invention can in general be referred to as a decarboxylation reaction. Suitable decarboxylation catalysts which can be employed in step (ii) include one or more metal oxides. A magnesium:aluminum mixed metal oxide is a preferred metal oxide catalyst as more fully described below. Both homogeneous and heterogeneous catalysts can be employed in the step (ii) reaction. The amount of decarboxylation catalyst used in step (ii) is not narrowly critical and is dependent on whether step (ii) is conducted batchwise or continuously. If batchwise, the catalyst employed can range from about 0.01 weight percent or less to about 10 weight percent or greater of the total weight of the starting materials. If continuously, generally a fixed bed is employed.

Suitable decarboxylation catalysts for use in the processes of this invention comprise one or more metal oxides, preferably mixed metal oxides containing two or more metal oxides. Illustrative of such metal oxides include, for example, one or more of the following: Group IA metal oxides, Group IIA metal oxides, Group IIIB metal oxides (including lanthanides and actinides), Group IVB metal oxides, Group VB metal oxides, Group VIB metal oxides, Group VIIB metal oxides, Group VIII metal oxides, Group IB metal oxides, Group IIB metal oxides, Group IIIA metal oxides, Group IVA metal oxides, Group VA metal oxides or Group VIA metal oxides. Certain of these metal oxides may also be used as transesterification catalysts in accordance with this invention such as Group IIA and IIIA metal oxides. Preferred metal oxides and mixed metal oxides are amphoteric or basic. Preferred metal oxides which may be utilized as decarboxylation catalysts include, for example, one or more oxides of magnesium, aluminum, calcium, strontium, gallium, beryllium, barium, scandium, yttrium, lanthanum, cerium, gadolinium, terbium, dysprosium, holmium, erbium, thulium, lutetium, ytterbium, niobium, tantalum, chromium, molybdenum, tungsten, titanium, zirconium, hafnium, vanadium, iron, cobalt, nickel, zinc, silver, cadmium, boron, indium, silicon, germanium, tin, lead, arsenic, antimony and bismuth.

Group IIA metal oxides such as magnesium oxide and calcium oxide and Group IIIA metal oxides such as aluminum oxide and gallium oxide are preferred mixed metal oxides for use in this invention. For mixed metal oxides in which at least one of the metals is magnesium, suitable metals in association with magnesium may include, for example, one or more of the following: Group IIIA metals such as boron, aluminum, gallium and indium, Group IIIB metals such as scandium, yttrium and lanthanum including the lanthanides, Group VB metals such as niobium and tantalum, Group VIB metals such as chromium, molybdenum and tungsten, Group VIII metals such as iron, cobalt and nickel, Group IIB metals such as zinc and cadmium, Group IVA metals such as silicon, germanium, tin and lead, Group VA metals such as arsenic, antimony and bismuth, and Group IVB metals such as zirconium and hafnium. For mixed metal oxides in which at least one of the metals is calcium, suitable metals in association with calcium may include, for example, one or more of the following: Group IIIA metals such as boron, aluminum, gallium and indium, Group IVA metals such as silicon, germanium, tin and lead, Group VB metals such as niobium and tantalum, and Group VIB metals such as chromium, molybdenum and tungsten.

Illustrative of mixed metal oxides which may be used as decarboxylation catalysts include, for example $MgO-Al_2O_3$, $MgO-SiO_2$, $MgO-CdO$, $MgO-Bi_2O_3$, $MgO-Sb_2O_5$, $MgO-SnO_2$, $MgO-ZrO_2$, $MgO-BeO$, $MgO-TiO_2$, $MgO-CaO$, $MgO-SrO$, $MgO-ZnO$, $MgO-Ga_2O_3$, $MgO-Y_2O_3$, $MgO-La_2O_3$, $MgO-MoO_3$, $MgO-Mn_2O_3$, $MgO-Fe_2O_3$, $MgO-Co_3O_4$, $MgO-WO_3$, $MgO-V_2O_5$, $MgO-Cr_2O_3$, $MgO-ThO_2$, $MgO-Na_2O$, $MgO-BaO$, $MgO-CaO$, $MgO-HfO_2$, $MgO-Li_2O$, $MgO-Nb_2O_5$, $MgO-Ta_2O_5$, $MgO-Gd_2O_3$, $MgO-Lu_2O_3$, $MgO-Yb_2O_3$, $MgO-CeO_2$, $MgO-Sc_2O_3$, $MgO-PbO$, $MgO-NiO$, $MgO-CuO$, $MgO-CoO$, $MgO-B_2O_3$, $CaO-SiO_2$, $CaO-Al_2O_3$, $CaO-SnO$, $CaO-PbO$, $CaO-Nb_2O_5$, $CaO-Ta_2O_5$, $CaO-Cr_2O_3$, $CaO-MoO_3$, $CaO-WO_3$, $CaO-TiO_2$, $CaO-HfO_2$, $MgO-SiO_2-Al_2O_3$, $MgO-SiO_2-ZnO$, $MgO-SiO_2-ZrO_2$, $MgO-SiO_2-CuO$, $MgO-SiO_2-CaO$, $MgO-SiO_2-Fe_2O_3$, $MgO-SiO_2-B_2O_3$, $MgO-SiO_2-WO_3$, $MgO-SiO_2-Na_2O$, $MgO-SiO_2-Ga_2O_3$, $MgO-SiO_2-La_2O_3$, $MgO-SiO_2-Nb_2O_5$, $MgO-SiO_2-Mn_2O_3$, $MgO-SiO_2-Co_3O_4$, $MgO-SiO_2-NiO$, $MgO-SiO_2-PbO$, $MgO-SiO_2-Bi_2O_3$, $MgO-Al_2O_3-ZnO$, $MgO-Al_2O_3-ZrO_2$, $MgO-Al_2O_3-Fe_2O_3$, $MgO-Al_2O_3-WO_3$, $MgO-Al_2O_3-La_2O_3$, $MgO-Al_2O_3-Co_3O_4$, $CaO-SiO_2-Al_2O_3$, $CaO-SiO_2-SnO$, $CaO-SiO_2-Nb_2O_5$, $CaO-SiO_2-WO_3$, $CaO-SiO_2-TiO_2$, $CaO-SiO_2-MoO_3$, $CaO-SiO_2-HfO_2$, $CaO-SiO_2-Ta_2O_5$, $CaO-Al_2O_3-SiO_2$, $CaO-Al_2O_3-PbO$, $CaO-Al_2O_3-Nb_2O_5$, $CaO-Al_2O_3-WO_3$, $CaO-Al_2O_3-TiO_2$, $CaO-Al_2O_3-MoO_3$, $CaO-HfO_2-Al_2O_3$, $CaO-HfO_2-TiO_2$, and the like. Other suitable mixed metal oxides embraced within the scope of this invention are disclosed by Tanabe et al., Bulletin of the Chemical Society of Japan, Vol. 47(5), pp. 1064-1066 (1974).

The metal oxides described herein which can be used as decarboxylation catalysts may contribute to product selectivity and/or catalytic activity of the reaction and/or stability of the catalyst. As discussed hereinafter, the decarboxylation catalyst employed in this invention may also contain support(s), binding agent(s) or other additives to stabilize or otherwise help in the manufacture of the catalyst.

The decarboxylation catalysts which comprise one or more metal oxides may be prepared in a wide variety of ways. For example, the one or more metal oxides can be provided from metal salts which can either be heated or precipitated to form the metal oxides. Also, one or more metal oxides may be provided as a partial condensate on a support, such as a silica or alpha, beta or gamma alumina, silicon carbide, and the like, and then condensed by heating to effect polymerization to the desired oxide form. The one or more metal oxides may be condensed from hydrolyzable monomers to the desired oxide(s), indeed, to form oxide powders which can thereafter be compressed in the presence of a condensation catalyst to form pellets and larger structures of the metal oxide decarboxylation catalyst. A blend of the powders and condensation catalyst can be made into a shapeable paste which can be extruded and cut into pellets according to conventional procedures. The extrudate may thereafter be fired to cure the condensation catalyst and fix the structure. The cut extrudate may be blended with a support material such as those characterized above, and the blend fired to fuse the metal oxide catalyst to the support.

In an embodiment of this invention, a magnesium salt, e.g., magnesium nitrate, and an aluminum salt, e.g., aluminum nitrate, are precipitated using ammonium hydroxide. The material is then washed with deionized water and calcined at a temperature of from about 350° C. to about 450° C. to afford the desired magnesium:aluminum mixed metal oxide catalyst.

In another embodiment, a magnesium oxide, e.g., magnesium carbonate hydroxide pentahydrate, and an aluminum oxide, e.g., aluminum hydroxide hydrate, are added to deionized water and thoroughly mixed to form a paste. The paste is then calcined at a temperature of from about 350° C. to about 450° C. to afford the desired magnesium:aluminum mixed metal oxide catalyst.

A preferred catalyst structure comprises a Group IIA and IIIA mixed metal oxide having a surface area of at least about 100 m$^2$/gm which may or may not be bonded to a support material. The decarboxylation catalysts on a support preferably have a surface area greater than about 20 m$^2$/gm to as high as about 260 m$^2$/gm, or greater depending upon which metal oxides are employed. In the case of magnesium:aluminum oxides, the surface area can be greater than about 50 m$^2$/gm to as high as about 260 m$^2$/gm, more preferably, greater than about 100 m$^2$/gm to as high as about 260 m$^2$/gm, determined according to the single point N$_2$ method.

The term "support," as used herein and in the claims, means a solid structure which does not adversely affect the catalytic properties of the catalyst and is at least as stable as the catalyst to the reaction medium. The support can function as a decarboxylation catalyst independent of the metal oxide catalyst used herein, although it may have lower catalytic activity to the reaction. The support may act in concert with the catalyst to moderate the reaction. Some supports may contribute to the selectivity of the reaction. The catalyst structure can comprise from about 2 to about 60 percent by weight or greater of the support, more preferably from about 10 to about 50 percent by weight of the support, the remainder being the weight of the metal oxide(s). Included in the weight of the support is the weight of any binding agent such as phosphates, sulfates, silicates, fluorides, and the like, and any other additive Provided to stabilize or otherwise help in the manufacture of the catalyst. The support may be Particles as large or larger than the catalyst component and "glued" to the decarboxylation catalyst by virtue of a binding medium.

The support may constitute a separate phase in the process of extruding the catalytic structure. In this embodiment, the support forming material, preferably as a paste is blended with a Paste of the decarboxylation catalyst or a partial condensate thereof. The paste may comprise the oxide forms of the support and the decarboxylation catalyst, each blended with water, and/or binding agents. The extrudate of the blend is passed through a multiorificed die and chopped into pellets of the desired sizes. The particles may be doughnut shaped, spherical, and the like. Then the particles are calcined to dry them and complete any condensation reaction in the support and/or the metal oxide decarboxylation catalyst.

A preferred group of mixed metal oxide catalysts for use in this invention include materials having the formula:

$$M_x^{2+}Q_y^{3+}(OH)_{2x+3y-nz}A_z^{n-}\cdot aH_2O \qquad (I)$$

wherein M is at least one divalent metal cation; Q is at least one trivalent metal cation; and A is at least one anion providing a valence (n−), wherein n is at least 1, e.g., between 1 and 4 and most often between 1 and 3, and wherein a is a positive number, M, Q, and A are provided in a proportion such that x/y is a number equal to or greater than 1, z has a value greater than zero and 2x+3y−nz is a positive number. M, Q and A may be selected to provide a layered structure. Preferably, x/y is in the range of 1 to 12, more preferably x/y is in the range of 1 to 6 and most preferably is in the range of 1 to 4. Preferably, z has a value such that x/z is between n and 12n, more preferably between n and 6n and most preferably between n and 4n.

Suitable divalent metal cations, M, broadly include elements selected from the Transition elements and Groups IIA and IVA of the Periodic Table as well as certain Group IIIB elements. As specific examples can be mentioned magnesium, calcium, titanium, vanadium, chromium, manganese, iron, cobalt, nickel, palladium, platinum, copper, zinc, cadmium, mercury, tin and lead. Divalent metal cations which are particularly suitable are magnesium, nickel, cobalt, zinc, calcium, strontium and copper. Suitable trivalent metal cations, Q, broadly include elements selected from the Transition elements and Groups IIIA and VA of the Periodic Table as well as certain Group IIIB elements. As specific examples can be mentioned aluminum, antimony, titanium, scandium, bismuth, vanadium, yttrium, chromium, iron, manganese, cobalt, ruthenium, nickel, gold, gallium, thallium, and cerium. Trivalent metal cations which are particularly suitable can be selected from aluminum, boron, gallium and lanthanum.

The composition of formula (I) also can include a wide range of anions, A. Any anion or combination of anions which can balance the charge of the cations can be used. Suitable anions include inter alia, halides (such as chloride, fluoride, bromide, and iodide), nitrite, nitrate, sulfite, sulfate, sulfonate, carbonate, chromate, cyanate, phosphite, phosphate, molybdocyanate, bicarbonate, hydroxide, arsenate, chlorate, ferrocyanide, borate, cyanide, cyanaurate, cyanaurite, ferricyanide, selenate, tellurate, bisulfate, as well as organic anions such as oxalate, acetate, hexanoate, sebacate, formate, benzoate, malonate, lactate, oleate, salicylate, stearate, citrate, tartrate, maleate, and the like. The class of metalate anions described in U.S. Pat. No. 4,667,045, including metavanadate, orthovanadate, molybdate, tungstate, hydrogen pyrovanadate and pyrovanadate, also are suitable as anion A. Anions suitable for use in combination with the metal cations previously identified as being particularly suitable are carbonate, halide, phosphate, chromate, sulfate, hydroxide, oxalate, acetate, nitrate, hexanoate, sebacate, vanadate, molybdate, tungstate and ferrocyanate.

The foregoing lists of suitable divalent and trivalent cations and suitable anions are meant to be illustrative and not exclusive. Those skilled in the art will recognize that other cations and anions can be used provided that the specific type of cations and their relative amounts (x/y ratio) and the specific type of anions and their relative amount result in a mixed metal oxide composition.

Included in the materials identified above are those based on exchangeable anionic clay minerals. For example, compositions of formula (I) wherein M is magnesium and Q is aluminum are related to hydrotalcites, while compositions in which M is nickel and A is aluminum are related to takovites. In fact, mixed metal oxides prepared using magnesium, nickel or cobalt as the divalent cation and aluminum as the trivalent cation exhibit the typical X-ray diffraction pattern of a hydrotalcite.

In a more preferred aspect, the processes of this invention can utilize mixed metal oxide catalyst compositions prepared by calcining at an elevated temperature compositions according to formula (I). Suitable calcined compositions have the general formula:

$$M_x^{2+}Q_y^{3+}(O)_{(2x+3y-nz)/2}D_z^{n-} \qquad (II)$$

wherein M, Q, x, y, z and n have the same meanings defined above in connection with formula (I), and D is at least one nonvolatile anion. Nonvolatile anions may include, inter alia, halides, nitrates, phosphites, phosphate, vanadate, molybdate, tungstate, sulfite, sulfate, chromate, arsenate, borate, chlorate and the like. This list is illustrative and not exclusive.

Heat treating the formula (I) compositions to prepare the calcined mixed metal oxide compositions of formula (II) can be done, for example, at a temperature in the range of 200° C. to 800° C. for a period of time of about 12 to 24 hours under an inert atmosphere such as nitrogen or in appropriate cases under an oxidizing atmosphere such as air.

Calcination of the mixed metal oxide composition dehydrates the composition and converts at least partially the metal hydroxides to metal oxides. Any nonvolatile anions may be present in the calcined material.

Provided the calcination temperature is not excessive, the mixed metal oxide can be rehydrated to the mixed metal hydroxide with water. Generally, the mixed metal oxide can be restored readily if the calcination temperature does not exceed about 600° C. Mixed metal oxides which are calcined under more severe conditions are not easily rehydrated and lower surface area materials are obtained.

Certain compositions falling within formula (I), such as hydrotalcite, which comprises a magnesium-aluminum hydroxide carbonate, and takovite, which comprises a nickel-aluminum hydroxide carbonate, are naturally occurring compositions. However, such compounds, as well as their related compositions, also can be prepared synthetically from inexpensive starting materials using well-known coprecipitation techniques. Procedures for direct synthesis of such materials are described in Itaya et al., *Inorg. Chem.* (1987)

26:624–626; Taylor, R. M., *Clay Minerals* (1984) 19:591–603; Reichle, U.S. Pat. No. 4,476,324; Bish, D. L., *Bull. Mineral* (1980), 103:170–175 and Miyata et al., *Clays and Clay Minerals* (1977), 25:14–18. Using direct synthesis one has the ability to vary within wide limits the $M^{+2}/Q^{+3}$ atomic ratio as well as the anion.

For example, a composition of formula (I) where $M^{+2}$ is nickel or magnesium, $Q^{+3}$ is aluminum and $A^{n-}$ is carbonate can be prepared by adding, as aqueous solutions, (a) a mixture of nitrates, sulfates or chlorides of nickel or magnesium and aluminum in a desired atomic ratio of nickel or magnesium to aluminum, e.g. 6 atoms of nickel as nickel chloride to 2 atoms of aluminum as aluminum chloride, to (b) an aqueous solution of a stoichiometric amount of sodium hydroxide and a water soluble salt of the desired anion, e.g., sodium carbonate. The two solutions are mixed at a temperature of about 25° C. to 35° C. with vigorous stirring over a several-hour period to produce a slurry. The slurry then is heated for about 18 hours at a temperature within the range of about 50° C. to 200° C. (preferably between about 60° C. to 75° C.) in order to control crystallization and the ultimate particle size of the resulting crystals. After filtering, and thorough washing and drying, the solids are recovered, typically as a powder.

As noted above, this procedure can be adapted to a wide variety of cations, cation atomic ratios and anion substitutions. For example, water soluble salts of divalent magnesium, cobalt, zinc, copper, iron and calcium can be substituted for the nickel chloride illustrated above, while water soluble salts of trivalent gallium and lanthanum can replace the aluminum chloride. A wide variety of other combinations also will be apparent to those skilled in the art. Generally, the rate of metal ion addition to the aqueous caustic/anion solution is not critical and can be varied widely. For example, a preferred preparation method is described in Schaper, H. et al., *Applied Catalysis*, 54, 1989, 79–90, the disclosure of which is incorporated herein by reference. The reaction temperature also is not critical, although the temperature during the reaction preferably is kept below about 100° C. An important feature of the procedure is the use of efficient agitation during the mixing procedure to avoid the formation of undesired by-products.

Loading of an anion A or D into the mixed metal oxide compositions is influenced by a variety of factors including (i) the amount of anion used in the preparation relative to the metal cations, (ii) the atomic ratio of the metal cations (x/y) in the preparation procedure, (iii) the size of the cations and anions and (iv) the preparation procedure. As used herein, "loading" is defined as the amount of available valences provided by a desired anion A or D expressed as a percentage of the total available valences for anion A or D. For example, carbonate loading in a hydrotalcite-type catalyst can be maximized by (i) using an excess (e.g., a greater than 3:1 molar ratio) of sodium carbonate to aluminum chloride during catalyst preparation and (2) adjusting the atomic ratio of magnesium to aluminum cations to about 2:1.

Mixed metal oxide compositions suitable as catalysts also can be prepared from the native or synthetic hydrotalcite-type compositions by ion exchange. For example, hydrotalcite can be treated at ambient conditions with 0.01N phosphoric acid for about 18 hours to replace the carbonate anion with phosphate anion. A halide analog of hydrotalcite prepared directly or by anion-exchange could be contacted with molybdic acid or a water soluble salt thereof, or with a water soluble salt of tungstic acid or vanadic acid in order to substitute the transition metal anion for the halide anion in the catalyst structure thereby to produce a mixed metal oxide composition of formula (I). Other ion exchanges will be apparent to those skilled in the art.

Calcined mixed metal oxide compositions may exhibit a higher level of selectivity/activity than uncalcined compositions. If a calcined mixed metal oxide catalyst composition experiences any decline in selectivity, it can be regenerated by a heat treatment in the presence of air to restore at least a portion of its initial level of selectivity/activity enhancement and reused. Conditions discussed above for calcining the hydrated mixed metal oxide compositions are suitable for regenerating compositions which have experienced a decline in activity.

Catalysts having the formulas (I) and (II) above wherein M is at least one of magnesium and calcium, Q is aluminum or gallium, A is at least one of carbonate, bicarbonate, phosphate, sulfate and nitrate, x/y is between 1 and 20, z has a value which satisfies the relationship: x/z is between n and 12n, and a is a positive number, are generally preferred for vapor phase decarboxylation due to their combination of activity (conversion of precursor) and selectivity. A preferred process involves a vapor phase process using mixed metal oxide catalyst wherein $M^{2+}$ is magnesium, $Q^{3+}$ is aluminum, $A^{n-}$ is carbonate, x/y is about 1, and z is about 1.

A group of preferred mixed metal oxide catalyst compositions which can be employed in the processes of this invention is disclosed in copending U.S. patent application Ser. No. 125,134, filed Nov. 25, 1987, now abandoned, the disclosure of which is incorporated herein by reference.

The step (ii) decarboxylation reaction may be effected in the liquid or vapor or supercritical liquid states or mixtures thereof. In this context, the vapor phase reaction is intended to refer to the general vapor state of the starting materials. Though the step (ii) decarboxylation reaction conditions may range from subatmospheric or atmospheric to superatmospheric conditions, it is desirable to run the step (ii) reaction from about 1 mm Hg to about 5,000 mm Hg, preferably from about 100 mm Hg to about 2,500 mm Hg.

The temperature of the step (ii) decarboxylation reaction may be as low as about 150° C. to about 500° C. Preferably, the reaction temperature ranges from about 175° C. to about 375° C., and most preferably from about 225° C. to about 350° C.

Suitable carboxylated ethers for use in the step (ii) decarboxylation reaction can be prepared by the step (i) transesterification reaction or by other methods such as the carbonylation of active hydrogen-containing compounds with carbon monoxide and oxygen at elevated temperatures in the presence of certain copper salts. Such a carbonylation process can be an alternative to the step (i) transesterification reaction and is encompassed within the generic scope of this invention. It is also appreciated that two or more $CO_2$ synthons can be reacted under conditions effective to produce a carboxylated ether.

The step (ii) decarboxylation reaction can be conducted in the presence of an inert diluent which can be either a liquid or gas. When a liquid diluent is employed, it should preferably be a good solvent for the starting materials, inert under the reaction conditions, and of such a nature that separation from the ether product will not be difficult. For instance, the boiling points of the diluent and the ether product should differ by an adequate amount and there should be no tendency of the diluent to form an azeotrope with the desired ether product.

Examples of useful liquid diluents that meet the foregoing qualifications include benzene, toluene, xylene, ethylbenzene, anisole, heptane, octane, nonane, decane, dibutyl ether, and the like. Hydrocarbons are preferred.

Illustrative gaseous diluents include for example, nitrogen, methane, hydrogen, carbon monoxide or carbon dioxide. The gaseous diluent should of course be chosen so that it does not prevent the preparation of the desired ether products.

While the use of such diluents may be beneficial, the processes of this invention can be operated using pure starting material(s) as a liquid or gaseous feed. The degree of dilution of the starting materials with various diluents may vary considerably depending upon any process constraints restricting the use of the diluent. For example, in commercial production, the use of very large quantities of some gaseous diluents may be disadvantageous due to the cost of pumping large volumes of the gaseous diluent and increased difficulty in isolating the ether product, which increase the energy costs of the process. With liquid diluents, the use of very large quantities may be disadvantageous due to the energy cost associated with large recovery and recycle. If the processes of this invention are to be carried out using a gaseous diluent, in general it is recommended that the starting material(s) constitute from about 1 to about 95, and preferably about 5 to about 50, mole percent of the starting material/carrier feed. Increasing the dilution of the starting material with a gaseous diluent such as hydrogen may tend to increase the selectivity of the reaction to the particular products desired. The amount of liquid diluent can vary widely, for instance, from no diluent to about 90 weight percent or greater of the total weight of the starting materials.

For processes of this invention in which a carboxylated ether is contacted with a metal oxide catalyst under conditions effective to produce an ether or an active hydrogen-containing compound and a $CO_2$ synthon are contacted in the presence of a metal oxide catalyst under conditions effective to produce an ether or other related processes described herein, it is understood that the process conditions described herein for the step (ii) decarboxylation reaction can desirably be employed for such processes.

The processes of this invention are useful for preparing substituted and unsubstituted ethers such as those embraced by the formulae $ROR_1$ or $ROR_2$ wherein R, $R_1$ and $R_2$ are as defined above. It is understood that the R and $R_1$ substituents together and the R and $R_2$ substituents together can complete a heterocycloalkyl ring which can be substituted or unsubstituted. Illustrative ethers prepared by the processes of this invention include, for example, dimethyl and diethyl ethers of polyethylene glycols, e.g., SELEXOL® materials, monoethylene glycol dimethyl or diethyl ether (glyme and ethyl glyme), diethylene glycol dimethyl or diethyl ether (diglyme and ethyl diglyme), triethylene glycol dimethyl or diethyl ether (triglyme and ethyl triglyme), tetraethylene glycol dimethyl or diethyl ether (tetraglyme and ethyl tetraglyme), polyethylene glycol dimethyl or diethyl ethers (polyglymes and ethyl polyglymes), bisglycidyl ether, polyethylene glycol diisopropyl ethers, polyethylene glycol dibutyl ethers, polyethylene glycol diallyl ethers, methyl-capped and ethyl-capped polyoxyalkylene materials, cellulose ethers and the like.

Illustrative of suitable ethers which can be prepared by the processes of this invention include those permissible ethers, including any permissible derivatives of described ethers, which are described in Kirk-Othmer, Encyclopedia of Chemical Technology, Third Edition, 1984, the pertinent portions of which are incorporated herein by reference.

The ether products produced by the processes of this invention can be separated by distillation. For example, a crude reaction product can be subjected to a distillation-separation at atmospheric or reduced pressure through a packed distillation column. Reactive distillation may be useful in conducting the step (i) transesterification reaction.

The processes of this invention may be carried out using, for example, a fixed bed reactor, a fluid bed reactor, or a slurry reactor. The optimum size and shape of the catalyst will depend on the type of reactor used. In general, for fluid bed reactors, a small, spherical catalyst particle is preferred for easy fluidization. With fixed bed reactors, larger catalyst particles are preferred so the back pressure within the reactor is kept reasonably low.

The processes of this invention can be conducted in a batch or continuous fashion, with recycle of unconsumed starting materials if required. The reaction can be conducted in a single reaction zone or in a plurality of reaction zones, in series or in parallel or it may be conducted batchwise or continuously in an elongated tubular zone or series of such zones. The materials of construction employed should be inert to the starting materials during the reaction and the fabrication of the equipment should be able to withstand the reaction temperatures and pressures. Means to introduce and/or adjust the quantity of starting materials or ingredients introduced batchwise or continuously into the reaction zone during the course of the reaction can be conveniently utilized in the processes especially to maintain the desired molar ratio of the starting materials. The reaction steps may be effected by the incremental addition of one of the starting materials to the other. Also, the reaction steps can be combined by the joint addition of the starting materials to the decarboxylation catalyst. When complete conversion is not desired or not obtainable, the starting materials can be separated from the ether product, for example by distillation, and the starting materials then recycled back into the reaction zone.

The processes are conducted for a period of time sufficient to produce the ethers. The exact reaction time employed is dependent, in part, upon factors such as temperature, nature and proportion of starting materials, and the like. The reaction time will normally be within the range of from about one-half to about 100 hours or more, and preferably from less than about one to about ten hours.

The processes may be conducted in either glass lined, stainless steel or similar type reaction equipment. The reaction zone may be fitted with one or more internal and/or external heat exchanger(s) in order to control undue temperature fluctuations, or to prevent any possible "runaway" reaction temperatures.

Illustrative of suitable reactants in effecting the processes of this invention include by way of example:

DMC—dimethyl carbonate
DEC—diethyl carbonate
MCA—2-(2-methoxyethoxy)ethanol

BCA—2-(2-butoxyethoxy)ethanol
MCE—2-methoxyethanol
AA—allyl alcohol
EG—ethylene glycol
DEG—diethylene glycol
TEG—triethylene glycol
TAEG—tetraethylene gylcol
PAEG—pentaethylene glycol
HEG—hexaethylene glycol
PEG—CARBOWAX®poly(oxyethylene)glycols
MPEG—alkoxy or allyloxy CARBOWAX® poly(oxyethylene)glycols
MHP—1-methoxy-2-hydroxypropane
IPA—2-propanol
PGS—polyethylene glycols
POLX—POLYOX® poly(oxyethylene)glycols
TER—TERGITOL® nonionic surfactants
UC—UCON® fluids and lubricants
DEA—diethanolaine
MEA—monoethanolamine
TEA—triethanolamine
MGMC—monoethylene glycol dimethyl carbonate
DGMC—diethylene glycol dimethyl carbonate
TIGMC—triethylene glycol dimethyl carbonate
TAGMC—tetraethylene glycol dimethyl carbonate
PAGMC—pentaethylene glycol dimethyl carbonate
HGMC—hexaethylene glycol dimethyl carbonate
PGMC—polyethylene glycol dimethyl carbonates
BBC—bis(2-butoxyethyl)carbonate
BGC—bisglycidyl carbonate
GLY—glycidol
BE—2-butoxyethanol
DAC—diallyl carbonate
MGEC—monoethylene glycol diethyl carbonate
DGEC—diethylene glycol diethyl carbonate
TIGEC—triethylene glycol diethyl carbonate
TAGEC—tetraethylene glycol diethyl carbonate
PAGEC—pentaethylene glycol diethyl carbonate
HGEC—hexaethylene glycol diethyl carbonate
PGEC—polyethylene glycol diethyl carbonates
PGPC—polyethylene glycol diisopropyl carbonates
PGBC—polyethylene glycol dibutyl carbonates
PGAC—polyethylene glycol diallyl carbonates
DEPC—2-(N,N-dimethyl)ethyl phenyl carbonate
OMC—n-octyl methyl carbonate
CMC—cyclohexyl methyl carbonate
BMEC—bis(2-morpholinoethyl)carbonate
CC—cellulose carbonates Illustrative of suitable products prepared by the processes of this invention include by way of example:
DMP—1,2-dimethoxypropane
DAE—diallyl ether
MGME—monoethylene glycol dimethyl ether (glyme)
DGME—diethylene glycol dimethyl ether (diglyme)
TIGME—triethylene glycol dimethyl ether (triglyme)
TAGME—tetraethylene glycol dimethyl ether (tetraglyme)
PAGME—pentaethylene glycol dimethyl ether (pentaglyme)
HGME—hexaethylene glycol dimethyl ether (hexaglyme)
PGME—polyethylene glycol dimethyl ethers (polyglymes)
DGDE—diethylene glycol dibutyl ether
BGE—bisglycidyl ether
MGEE—monoethylene glycol diethyl ether (ethyl glyme)
DGEE—diethylene glycol diethyl ether (ethyl diglyme)
TIGEE—triethylene glycol diethyl ether (ethyl triglyme)
TAGEE—tetraethylene glycol diethyl ether (ethyl tetraglyme)
PAGEE—pentaethylene glycol diethyl ether (ethyl pentaglymes)
HGEE—hexaethylene glycol diethyl ether (ethyl hexaglymes)
PGEE—polyethylene glycol diethyl ethers (ethyl polyglymes)
PGPE—polyethylene glycol diisopropyl ethers (isopropyl polyglymes)
PGBE—polyethylene glycol dibutyl ethers
PGAE—polyethylene glycol diallyl ethers
DEPE—2-(N,N-dimethyl)ethyl phenyl ether
OME—n-octyl methyl ether
CME—cyclohexyl methyl ether
BMEE—bis(2-morpholinoethyl)ether
CE—cellulose ethers Illustrative of permissible reactions encompassed within the scope of this invention include, for example, the following reactant/product combinations:

| REACTANT(S) | PRODUCT(S) |
|---|---|
| DMC, MCA | TAGME |
| DMC, MCA | DGME |
| DMC, MCE | MGME |
| DMC, AA | DAE |
| MHP, DMC | DMP |
| EG, DMC | MGME |
| DEG, DMC | DGME |
| TEG, DMC | TIGME |
| TAEG, DMC | TAGME |
| PAEG, DMC | PAGME |
| HEG, DMC | HGME |
| MPEG, DMC | PGME |
| PEG, DMC | PGME |
| BE, DMC | DCE |
| GLY, DMC | BGE |
| DAC | DAE |
| MGMC | MGME |
| DGMC | DGME |
| TIGMC | TIGME |
| TAGMC | TAGME |
| PAGMC | PAGME |
| HGMC | HGME |
| PGMC | PGME |
| BGC | BGE |
| BBC | DGDE |
| MGEC | MGEE |
| DGEC | DGEE |
| TIGEC | TIGEE |
| TAGEC | TAGEE |
| PAGEC | PAGEE |
| HGEC | HGEE |
| PGEC | PGEE |
| PGPC | PGPE |
| PGBC | PGBE |
| PGAC | PGAE |
| DEPC | DEPE |
| OMC | OME |
| CMC | CME |
| BMEC | BMEE |

As used herein, the phrase "residue of an organic compound" is contemplated to include all permissible residues of organic compounds. In a broad aspect, the permissible residues include acyclic and cyclic, branched and unbranched, carbocyclic and heterocyclic, aromatic and nonaromatic residues of organic compounds. Illustrative organic compound residues include, for example, alkyl, aryl, cycloalkyl, heterocycloalkyl, alkyl(oxyalkylene), aryl(oxyalkylene), cycloalkyl(oxyalkylene), heterocycloalkyl(oxyalkylene), hydroxy(alkyleneoxy) and the like. The permissible residues can be substituted or unsubstituted and the same or different for appropriate organic compounds. This invention is not intended to be limited in any manner by the permissible residues of organic compounds.

As used herein, the term "substituted" is contemplated to include all permissible substituents of organic compounds. In a broad aspect, the permissible substituents include acyclic and cyclic, branched and unbranched, carbocyclic and heterocyclic, aromatic and nonaromatic substituents of organic compounds. Illustrative substituents include, for example, alkyl, alkyloxy, aryl, aryloxy, hydroxy, hydroxyalkyl, amino, aminoalkyl, halogen and the like in which the number of carbons can range from 1 to about 20 or more, preferably from 1 to about 12. The permissible substituents can be one or more and the same or different for appropriate organic compounds. This invention is not intended to be limited in any manner by the permissible substituents of organic compounds.

Certain of the following examples are provided to further illustrate the processes of this invention.

The following apparatus was used for the preparation of ethers in Examples 2-13 below. An Appied Test Systems, Inc. Model 3620 Split Test Oven equipped with a preheater (stainless steel ⅛ inch o.d.×2 feet) and ¼ inch (o.d.) stainless steel reactor tube (8 inch length) was packed with catalyst and heated to the desired reaction temperature using a Honeywell Dial-A-Trol temperature controller. The temperatures at the top of the reactor and the bottom were monitored using a digital temperature readout. The liquid feed was added (downflow) to the reactor via a Fluid Metering Inc. RP-G20 drive pump equipped with an ⅛ inch pump head. The system was maintained under nitrogen, which was introduced prior to the liquid preheater and was monitored with a rotometer. The product mixture was collected in a 100 milliliter round bottom flask, vented first to a dry ice/acetone trap and then a Firestone valve. Analysis was performed by capillary gas chromatography (FID) using a DB-1701 column.

EXAMPLE 1

Preparation of Decarboxylation Catalyst

A total of 44.1 grams of magnesium nitrate hexahydrate and 66.0 grams of aluminum nitrate nonahydrate were dissolved in 200 milliliters of distilled water to give a first solution. A total of 4.8 grams of ammonium carbonate was dissolved in 200 milliliters of concentrated ammonium hydroxide (28-29 weight percent) to give a second solution. About 100 milliliters of distilled water was heated in a flask at a temperature of 40° C. and the first and second solutions were combined simultaneously with good agitation using a mechanical stirrer. The rates of addition of the first and second solutions were adjusted to maintain a pH of 9-10. The total addition took 10 minutes and a final pH of 9.5 was obtained. The contents were stirred at a temperature of 40° C. for a period of 40 minutes. The resulting precipitate was filtered and washed (ca. 300 milliliters three to four times) with water at a temperature of 60° C. until the pH of the wash was neutral. The filter cake was dried at a temperature of 80° C. overnight. The weight of the dried filter cake was about 16 grams. The filter cake was then calcined in air at a temperature of 400° C. for a period of 3 hours to afford a magnesium:aluminum mixed metal oxide.

EXAMPLES 2-5

Preparation of Bis(2-butoxyethyl)carbonate

A total of 118.2 grams (1 mole) of 2-butoxyethanol, 120.1 grams (1.5 moles) of dimethyl carbonate, and 1.0 gram of potassium carbonate were combined in a 300 milliliter round bottom three-neck flask equipped with a straight distillation head and magnetic stirrer. The flask contents were heated to reflux at an initial temperature of 64° C. at the head and 89° C. in the kettle. A methanol/dimethyl carbonate azeotrope was slowly removed overhead. A total of 99.5 grams of material was removed overhead (64° C.-90° C.) over a period of about 13 hours, after which time the kettle temperature rose to 228° C. After this time, the flask contents were cooled (132.2 grams) and filtered into a 200 milliliter round bottom flask. The flask contents were then placed under vacuum. The desired product was collected at a temperature of 135° C.-142° C. at 6 mm Hg. A total of 96.6 grams (73.7 percent yield) of bis(2-butoxyethyl)carbonate was obtained at a purity of greater than 99 percent as analyzed by capillary gas chromatography on a DB-1701 column.

Preparation of Bis(2-butoxyethyl)ether

Bis(2-butoxyethyl)carbonate prepared above was passed through a catalyst bed containing 10.8 grams of a magnesium:aluminum mixed metal oxide (3/16 inch tablets, Mg/Al 3:1) at a reaction temperature indicated in Table A below and at a liquid feed rate of about 0.3 milliliters/minute. The feed was continued for a period of 1 hour and then analyzed by capillary gas chromatography on a DB-1701 column. The results are given in Table A.

TABLE A

| Preparation of Bis(2-butoxyethyl)ether | | | | |
|---|---|---|---|---|
| Example No. | 2 | 3 | 4 | 5 |
| Process Conditions Temperature, °C. | 225 | 225 | 250 | 300 |
| Product Composition, area % | | | | |
| 2-Butoxyethanol | 4.83 | 2.55 | 5.23 | 15.50 |
| Bis(2-butoxyethyl)-carbonate | 53.93 | 72.57 | 52.37 | 30.98 |
| Bis(2-butoxyethyl)-ether | 37.83 | 22.07 | 35.29 | 38.10 |

EXAMPLES 6-7

Preparation of Bis(sec-butyl)carbonate

Bis(sec-butyl)carbonate was prepared from 2-butanol and dimethyl carbonate via the following procedure. A total of 51.88 grams (0.7 mol) of 2-butanol, 64.22 grams (0.71 mol) of dimethyl carbonate, and 1.0 gram (0.003 mol) of di-n-butyltin dimethoxide were combined in a 250 milliliter 3-neck flask equipped with a distillation head and vigreaux column. The reaction mixture was refluxed under nitrogen overnight (kettle temperature 84° C., head temperature 80° C.). With a head temperature of 63° C. (kettle 74° C.), the condensate was taken over slowly. A total of 46.2 grams of distillate was collected while maintaining a head temperature of less than 73° C. A second distillate fraction of 5.7 grams was collected at a head temperature of 73°-94° C. At this point the relative amount of methyl sec-butyl carbonate to bis(sec-butyl)carbonate was about 2:1. The flask was cooled and an additional 14.8 grams (0.2 mol) of 2-butanol was added and the reaction mixture heated to reflux. The condensate was again taken over slowly at a head temperature less than 74° C. to afford an additional 13.7 grams of distillate. At this point the head temperature reached 133° C. and the kettle temperature was 169° C. A small distillate fraction (5.7 grams) was taken overhead followed by a second distillate fraction (53.5 grams) which contained bis(sec-butyl)carbonate (head temperature 161° C., kettle temperature 174° C.). Analysis by capillary gas chromotography showed 93% (area) purity of bis(sec-butyl)carbonate with 7% (area) methyl sec-butyl carbonate.

Preparation of Bis(sec-butyl)ether

Bis(sec-butyl)carbonate was passed through a catalyst bed containing 11.5 grams of a magnesium-:aluminum mixed metal oxide (3/16 inch tablets, Mg/Al 3:1) at a reaction temperature indicated in Table B below and at a liquid feed rate of about 0.3 milliliters/minute. The feed was continued for a period of 1 hour and then analyzed by capillary gas chromatography on a DB-1701 column. The results are given in Table B.

TABLE B

| Preparation of Bis(sec-butyl)ether | | |
|---|---|---|
| Example No. | 6 | 7 |
| Process Conditions Temperature, °C. | 250 | 275 |
| Product Composition, area % | | |
| Bis(sec-butyl)carbonate | 41.37 | 12.46 |
| Bis(sec-butyl)ether | 12.82 | 19.60 |

EXAMPLES 8-9

Preparation of Bis(2-methoxyethyl)carbonate

A total of 76.1 grams (1 mole) of 2-methoxyethanol, 67.6 grams (0.75 moles) of dimethyl carbonate, and 0.5 grams of dibutyltin dimethoxide were combined in a 250 milliliter round bottom three-neck flask equipped with a straight distillation head and a magnetic stirrer. The flask contents were heated to reflux at an initial temperature of 73° C. at the head and 102° C. in the kettle. After 7 minutes at reflux, a methanol/dimethyl carbonate azeotrope was slowly removed overhead. A total of 55.9 grams of material was removed overhead (64° C.-88° C.) over a period of about 21 hours after which time the kettle temperature rose to 145° C. After this time, the flask contents were cooled and put under vacuum. The desired product was collected at a temperature of 97° C.-105° C. at 3 mm Hg. A total of 77.98 grams (87.5 percent yield) of bis(2-methoxyethyl)carbonate was obtained at a purity of greater than 99 percent as analyzed by capillary gas chromatography on a DB-1701 column.

Preparation of Diethylene Glycol Dimethyl Ether

Bis(2-methoxyethyl)carbonate was passed through a catalyst bed containing 11.5 grams of a magnesium-:aluminum mixed metal oxide (3/16 inch tablets, Mg/Al 3:1) at a reaction temperature indicated in Table C below and at a liquid feed rate of about 0.3 milliliters/minute. The feed was continued for a period of 1 hour and analyzed by capillary gas chromography on a DB-1701 column. The results are given in Table C.

TABLE C

| Preparation of Diethylene Glycol Dimethyl Ether | | |
|---|---|---|
| | 8 | 9 |
| Process Conditions Temperature, °C. | 250 | 275 |
| Product Composition, area % | | |
| 2-Methoxyethanol | 5.77 | 7.62 |
| Monoethylene glycol dimethyl ether | 5.27 | 5.54 |
| Bis(2-methoxyethyl)-carbonate | 62.23 | 63.65 |
| Diethylene glycol dimethyl ether | 23.30 | 23.18 |

EXAMPLE 10

Preparation of Cyclohexyl Methyl Ether

A mixture of cyclohexanol (1 mole) and dimethyl carbonate (3 mole) was passed through 11.5 grams of a magnesium:aluminum mixed metal oxide (3/16 inch pellets, Mg/Al 3:1) at a temperature of 250° C. and at a liquid feed rate of 0.32 milliliters/minute. After a period of one hour, a total of 31 grams of liquid was collected. Analysis was performed by capillary gas chromatography (FID) using a DB-1701 column. The results were (area %) as follows:
  5.9% methanol
  3.0% dimethyl carbonate
  77.3% cyclohexyl methyl ether
  7.1% cyclohexanol.

EXAMPLE 11

Preparation of Diethylene Glycol Diethyl Ether

A mixture of 2-(2-ethoxyethoxy)ethanol (1 mole) and diethyl carbonate (3 mole) was passed through 11.5 grams of a magnesium:aluminum mixed metal oxide (3/16 inch pellets, Mg/Al 3:1) at a temperature of 225° C. and at a liquid feed rate of 0.29 milliliters/minute. After a period of one hour, a total of 30.2 grams of liquid was collected. Analysis was performed by capillary gas chromatography (FID) using a DB-1701 column. The results were (area %) as follows:
  19.1% diethyl ether
  16.0% ethanol
  14.3% diethyl carbonate
  41.2% diethylene glycol diethyl ether
  3.3% tetraethylene glycol diethyl ether.

EXAMPLE 12

Preparation of n-Decyl Methyl Ether

A mixture of 1-decanol (1 mole) and dimethyl carbonate (3 mole) was passed through 11.5 grams of a magnesium:aluminum mixed metal oxide (3/16 inch pellets, Mg/Al 3:1) at a temperature of 250° C. and at a liquid feed rate of 0.34 milliliters/minute. After a period of 1.1 hour, a total of 36.5 grams of liquid was collected. Analysis was performed by capillary gas chromatography (FID) using a DB-1701 column. The results were (area %) as follows:
  2.5% methanol
  0.7% dimethyl carbonate
  75.6% n-decyl methyl ether
  9.0% 1-decanol
  2.2% n-decyl methyl carbonate
  4.5% bis(n-decyl)ether.

EXAMPLE 13

Preparation of 1,2-Dimethoxypropane (Propylene Glycol Dimethyl Ether)

A mixture of 1-methoxy-2-propanol (1 mole) and dimethyl carbonate (4 mole) was passed through 11.5 grams of a magnesium:aluminum mixed metal oxide (3/16 inch pellets, Mg/Al 3:1) at a temperature of 250° C. and at a liquid feed rate of 0.35 milliliters/minute. After a period of 1 hour, a total of 30.6 grams of liquid was collected. Analysis was performed by capillary gas chromatography (FID) using a DB-1701 column. The results were (area %) as follows:
  12.5% methanol
  0.6% dimethyl carbonate
  75.7% propylene glycol dimethyl ether
  8.7% 1-methoxy-2-propanol.

EXAMPLES 14–22

Preparation of Methyl 2-(2-Methoxyethoxy)ethyl Carbonate

A total of 144.2 grams (1.2 mol) of 2-(2-methoxyethoxy)ethanol, 400 grams (4.4 mol) of dimethyl carbonate and 3 grams (0.05 mol) of sodium methoxide were combined in a 1-liter 3-neck round bottom flask equipped with a 14 inch distillation column, distillation head, and magnetic stirbar. The system was evacuated and purged three times with nitrogen using a Firestone valve, and left under a constant nitrogen atmosphere. After a period of 1.5 hours at reflux (kettle temperature 84° C.), methanol (boiling point 64° C.) was slowly removed overhead to drive the equilbrium. A total of 49.8 grams of methanol was removed over a period of 3 hours, after which time the stopcock was closed and the reaction mixture was allowed to reflux overnight. The mixture was then cooled to room temperature, filtered and charged (429 grams) to a 500 milliliter round bottom flask equipped with a distillation head and magnetic stirbar. Excess dimethyl carbonate (boiling point 90° C.) was removed overhead. The flask was then cooled, put under vacuum (10–11 mm Hg, and methyl 2-(2-methoxyethoxy)ethyl carbonate removed overhead (boiling point 115°–125° C.). A total of 193 grams (ca. 90% yield) was obtained. Gas chromatography analysis of this material showed 97.74% purity (remainder was 2-(2-methoxyethoxy)ethanol).

Preparation of Diethylene Glycol Dimethyl Ether and Tetraethylene Glycol Dimethyl Ether Chunks of magnesium:aluminum mixed metal oxide (Mg/Al 3:1) materials were crushed to a fine powder and calcined at a temperature of 400° C. overnight. A total of 2.5 grams of the calcined magnesium:aluminum mixed metal oxide (Mg/Al 3:1) materials was charged to a 7.5 inch stainless steel tube (3/8 inch o.d.) which was then connected to a preheater installed in a Hewlett Packard GC oven. The temperature was set at 275° C. and, after reaching reaction temperature, the methyl 2-(2-methoxyethoxy)-ethyl carbonate prepared above (generally 10 grams) was fed via a FMI piston pump at 0.5 milliliters/minute with a nitrogen sweep. The material at the reactor outlet was allowed to condense in a sample bottle (cooled in dry ice/acetone) equipped with an outlet vented to the hood. Products were analyzed on a gas chromatograph and the results are given in Table D below.

TABLE D

| | Preparation of Diglyme and Tetraglyme | | | | | | | | |
|---|---|---|---|---|---|---|---|---|---|
| Example No. | 14 | 15 | 16 | 17 | 18 | 19 | 20 | 21 | 22 |
| Catalyst Composition Mg/Al ratio | 2/1 | 2/1 | 3/1 | 4/1 | 5/1 | 3/1 | *3/3/1 | **3/3/1 | 5/1 |
| Product Composition, Area % | | | | | | | | | |
| Methyl Carbitol | 20.50 | 0.72 | 0.80 | 15.95 | 7.48 | 1.21 | 10.46 | 8.42 | 25.05 |
| Dimethyl Carbonate | 7.95 | 0.00 | 0.00 | 2.39 | 1.54 | 0.46 | 3.85 | 4.09 | 0.00 |
| Methyl 2-(2-methoxyethoxy)-ethyl carbonate | 36.87 | 0.31 | 0.42 | 7.66 | 0.21 | 0.36 | 18.22 | 9.23 | 0.22 |
| Bis[2-(2-methoxyethoxy)-ethyl]carbonate | 19.34 | 0.00 | 0.00 | 3.35 | 0.00 | 0.00 | 9.80 | 4.01 | 0.00 |
| Diethylene glycol dimethyl ether (Diglyme) | 12.13 | 82.32 | 82.07 | 57.17 | 77.95 | 84.32 | 44.28 | 60.31 | 71.62 |
| Tetraethylene glycol dimethyl ether (Tetraglyme) | 2.18 | 14.84 | 15.07 | 10.27 | 12.14 | 11.54 | 11.37 | 11.91 | 1.94 |
| Unknowns | 1.03 | 1.81 | 1.64 | 3.21 | 0.68 | 2.11 | 2.02 | 2.03 | 1.17 |

*Co/Mg/Al
**Ni/Mg/Al

Although the invention has been illustrated by certain of the preceding examples, it is not to be construed as being limited thereby; but rather, the invention encompasses the generic area as hereinbefore disclosed. Various modifications and embodiments can be made without departing from the spirit and scope thereof.

We claim:

1. A process for preparing ethers which comprises contacting a carboxylated ether with a metal oxide catalyst under decarboxylation conditions effective to produce the ether.

2. The process of claim 1 wherein the carboxylated ether comprises a substituted or unsubstituted carboxyl-containing ether compound.

3. The process of claim 2 wherein the carboxylated ether comprises a material having the formulae:

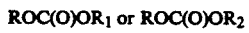

ROC(O)OR$_1$ or ROC(O)OR$_2$ wherein R is the residue of an organic compound, R$_1$ is the residue of an organic compound, and R$_2$ is the residue of an organic compound.

4. The process of claim 2 wherein the carboxylated ether comprises a material having the formula:

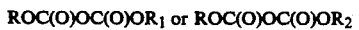

ROC(O)OC(O)OR$_1$ or ROC(O)OC(O)OR$_2$ wherein R is the residue of an organic compound, R₁ is the residue of an organic compound, and R₂ is the residue of an organic compound.

5. The process of claim 1 wherein the metal oxide catalyst comprises one or more Group IIA metal oxides, Group IIIB metal oxides, Group IVB metal oxides, Group VB metal oxides, Group VIB metal oxides, Group VIIB metal oxides, Group VIII metal oxides, Group IB metal oxides, Group IIB metal oxides, Group IIIA metal oxides, Group IVA metal oxides, Group VA metal oxides or Group VIA metal oxides.

6. The process of claim 5 wherein the metal oxide catalyst comprises one or more oxides of magnesium, aluminum, calcium, strontium, gallium, beryllium, barium, scandium, yttrium, lanthanum, cerium, gadolinium, terbium, dysprosium, holmium, erbium, thulium, lutetium, ytterbium, niobium, tantalum, chromium, molybdenum, tungsten, titanium, zirconium, hafnium, vanadium, iron, cobalt, nickel, zinc, silver, cadmium, boron, indium, silicon, germanium, tin, lead, arsenic, antimony and bismuth.

7. The process of claim 1 wherein the metal oxide catalyst comprises at least one Group IIA metal oxide.

8. The process of claim 1 wherein the metal oxide catalyst comprises a Group IIA metal oxide and a Group IIIA metal oxide.

9. The process of claim 1 wherein the metal oxide catalyst comprises a Group IIA metal oxide and a Group IIIB metal oxide.

10. The process of claim 1 wherein the metal oxide catalyst comprises magnesium oxide and aluminum oxide.

11. The process of claim 1 wherein the metal oxide catalyst comprises a mixed metal oxide.

12. The process of claim 1 wherein the metal oxide catalyst has a surface area greater than about 50 m²/gm.

13. The process of claim 7 wherein the Group IIA metal oxide comprises from about 10 weight percent to about 90 weight percent of the weight of the catalyst.

14. The process of claim 1 wherein the metal oxide catalyst is associated with a support material.

15. The process of claim 14 wherein the support comprises an alumina material or an alumina-silica material.

16. The process of claim 14 wherein the support comprises an silica material or a silica-alumina material.

17. The process of claim 14 wherein the support comprises from about 2 to about 50 percent by weight of the metal oxide catalyst.

18. The process of claim 1 wherein the metal oxide catalyst comprises
(a) a material having the formula $$M_x^{2+}Q_y^{3+}(OH)_{2x+3y-nz}A_z^{n-}\cdot aH_2O \qquad (I)$$

wherein M is at least one divalent metal cation; Q is at least one trivalent metal cation; and A is at least one anion providing a valence (n−), wherein n is 1 to 4 and wherein a is a positive number, M, Q and A are provided in a proportion such that x/y is a number equal to or greater than 1, z has a value greater than zero and 2x+3y−nz is a positive number, or
(b) a material prepared by calcining the material of formula (I) having the formula $$M_x^{2+}Q_y^{3+}(O)_{(2x+3y-nz)/2}D_z^{n-} \qquad (II)$$

wherein M, Q, x, y, z and n have the same meanings defined above in connection with formula (I), and D is at least one nonvolatile anion.

19. The process of claim 18 wherein x/y is a number between 1 and 12 and z has a value which satisfies the relationship: x/z is between n and 12n.

20. The process of claim 18 wherein A is selected from the group consisting of carbonate, halide, phosphite, phosphate, chromate, sulfate, hydroxide, oxalate, acetate, nitrate, hexanoate, sebacate, vanadate, molybdate, tungstate and ferrocyanate.

21. The process of claim 18 wherein D is selected from the group consisting of halides, phosphite, phosphate, vanadate, molybdate, tungstate, sulfite, sulfate, chromate, arsenate, borate and chlorate.

22. The process of claim 18 wherein x/y is a number between 1 and 6 and z has a value which satisfies the relationship: x/z is between n and 6n.

23. The process of claim 18 wherein said material prepared by calcining the material of formula (I) has been heat treated at a temperature in the range of 200° C. to 800° C. for 12 to 24 hours.

24. The process of claim 18 wherein M is magnesium and and Q is aluminum.

25. The process of claim 1 wherein the ether comprises a substituted or unsubstituted ether.

26. The process of claim 1 wherein the ether comprises a material having the formula:

ROR₁ wherein R is the residue of an organic compound, and R₁ is the residue of an organic compound.

27. The process of claim 1 wherein the ether comprises a material having the formula:

ROR₂ wherein R is the residue of an organic compound, and R₂ is the residue of an organic compound.

28. A process for preparing ethers which comprises (i) contacting an active hydrogen-containing compound with a CO₂ synthon under transesterfication conditions effective to produce a carboxylated ether, and (ii) contacting the carboxylated ether with a metal oxide catalyst under decarboxylation conditions effective to produce the ether. with a metal oxide catalyst under conditions effective to produce the ether.

29. The process of claim 28 wherein the active hydrogen-containing compound comprises a substituted or unsubstituted alcohol, phenol, carboxylic acid, amine, thiophenol, mercaptan or amide.

30. The process of claim 28 wherein the active hydrogen-containing compound is selected from the group consisting of substituted and unsubstituted monohydric, dihydric and polyhydric alcohols.

31. The process of claim 30 wherein the hydroxyl-containing compound comprises 2-(2-methoxyethoxy)ethanol, 2-(2-butoxyethoxy)-ethanol, 2-methoxyethanol, a poly(oxyalkylene) glycol, ethylene glycol, diethylene glycol, triethylene glycol, tetraethylene glycol, pentaethylene glycol, hexaethylene glycol, a poly(oxyethylene)(oxypropylene)glycol, an alkoxy or allyloxy poly(oxyalkylene)glycol, an alkoxy or allyloxy poly(oxyethylene)(oxypropylene)glycol, a polyethylene glycol, diethanolamine, triethanolamine, monoethanolamine or 1-methoxy-2-hydroxypropane.

32. The process of claim 28 wherein the CO₂ synthon comprises a substituted or unsubstituted carbonate, chlorocarbonate, carbonic acid, carbamate, carbamic acid, oxalate, 2-oxazolidinone, urea, ester, phosgene, chloroformate, carbon dioxide, orthocarboxylate, sulfurous acid or sulfurous acid ester.

33. The process of claim 28 wherein the $CO_2$ synthon comprises dimethyl carbonate or diethyl carbonate.

34. The process of claim 28 wherein the carboxylated ether comprises a substituted or unsubstituted carboxyl-containing ether compound.

35. The process of claim 28 wherein the carboxylated ether comprises monoethylene glycol dimethyl or diethyl or diallyl carbonate, diethylene glycol dimethyl or diethyl or diallyl carbonate, triethylene glycol dimethyl or diethyl or diallyl carbonate, tetraethylene glycol dimethyl or diethyl or diallyl carbonate, a polyethylene glycol dimethyl or diethyl or diallyl carbonate, bisglycidyl carbonate, a polyethylene glycol diisopropyl carbonate or a polyethylene glycol dibutyl carbonate.

36. The process of claim 28 wherein the metal oxide catalyst comprises one or more Group IA metal oxides, Group IIA metal oxides, Group IIIB metal oxides, Group IVB metal oxides, Group VB metal oxides, Group VIB metal oxides, Group VIIB metal oxides, Group VIII metal oxides, Group IB metal oxides, Group IIB metal oxides, Group IIIA metal oxides, Group IVA metal oxides, Group VA metal oxides or Group VIA metal oxides.

37. The process of claim 36 wherein the metal oxide catalyst comprises one or more oxides of magnesium, aluminum, calcium, strontium, gallium, beryllium, barium, scandium, yttrium, lanthanum, cerium, gadolinium, terbium, dysprosium, holmium, erbium, thulium, lutetium, ytterbium, niobium, tantalum, chromium, molybdenum, tungsten, titanium, zirconium, hafnium, vanadium, iron, cobalt, nickel, zinc, silver, cadmium, boron, indium, silicon, germanium, tin, lead, arsenic, antimony and bismuth.

38. The process of claim 28 wherein the metal oxide catalyst comprises at least one Group IIA metal oxide.

39. The process of claim 28 wherein the metal oxide catalyst comprises a Group IIA metal oxide and a Group IIIA metal oxide.

40. The process of claim 28 wherein the metal oxide catalyst comprises a Group IIA metal oxide and a Group IIIB metal oxide.

41. The process of claim 28 wherein the metal oxide catalyst comprises magensium oxide and aluminum oxide.

42. The process of claim 28 wherein the metal oxide catalyst comprises mixed metal oxide.

43. The process of claim 28 wherein the ether comprises a substituted or unsubstituted ether.

44. The process of claim 28 wherein the ether comprises monoethylene glycol dimethyl or diethyl ether, diethylene glycol dimethyl or diethyl ether, triethylene glycol dimethyl or diethyl ether, tetraethylene glycol dimethyl or diethyl ether, a polyethylene glycol dimethyl or diethyl ether, bisglycidyl ether, a polyethylene glycol diisopropyl ether, a polyethylene glycol dibutyl ether or a polyethylene glycol diallyl ether.

45. A process for preparing ethers which comprises contacting an active hydrogen-containing compound with a $CO_2$ synthon in the presence of a metal oxide catalyst under decarboxylation conditions effective to produce the ether.

46. The process of claim 45 wherein the active hydrogen-containing compound comprises a substituted or unsubstituted alcohol, phenol, carboxylic acid, amine, thiophenol, mercaptan or amide.

47. The process of claim 45 wherein the active hydrogen-containing compound is selected from the group consisting of substituted and unsubstituted monohydric, dihydric and polyhydric alcohols.

48. The process of claim 47 wherein active hydrogen-containing compound comprises 2-(2-methoxyethoxy)ethanol, 2-(2-butoxyethoxy)-ethanol, 2-methoxyethanol, a poly(oxyalkylene)-glycol, ethylene glycol, diethylene glycol, triethylene glycol, tetraethylene glycol, pentaethylene glycol, hexaethylene glycol, a poly(oxyethylene)(oxypropylene)glycol, an alkoxy or allyloxy poly(oxyalkylene)glycol, an alkoxy or allyloxy poly(oxyethylene)(oxypropylene)glycol, a polyethylene glycol, diethanolamine, triethanolamine, monoethanolamine or 1-methoxy-2-hydroxypropane.

49. The process of claim 45 wherein the $CO_2$ synthon comprises a substituted or unsubstituted carbonate, chlorocarbonate, carbonic acid, carbamate, carbamic acid, oxalate, 2-oxazolidinone, urea, ester, phosgene, choroformate, carbon dioxide, orthocarboxylate, sulfurous acid or sulfurous acid ester.

50. The process of claim 45 wherein the $CO_2$ synthon comprises dimethyl carbonate or diethyl carbonate.

51. The process of claim 45 wherein the metal oxide catalyst comprises one or more Group IA metal oxides, Group IIA metal oxides, Group IIIB metal oxides, Group IVB metal oxides, Group VB metal oxides, Group VIB metal oxides, Group VIIB metal oxides, Group VIII metal oxides, Group IB metal oxides, Group IIB metal oxides, Group IIIA metal oxides, Group IVA metal oxides, Group VA metal oxides or Group VIA metal oxides.

52. The process of claim 51 wherein the metal oxide catalyst comprises one or more oxides of magnesium, aluminum, calcium, strontium, gallium, beryllium, barium, scandium, yttrium, lanthanum, cerium, gadolinium, terbium, dysprosium, holmium, erbium, thulium, lutetium, ytterbium, niobium, tantalum, chromium, molybdenum, tungsten, titanium, zirconium, hafnium, vanadium, iron, cobalt, nickel, zinc, silver, cadmium, boron, indium, silicon, germanium, tin, lead, arsenic, antimony and bismuth.

53. The process of claim 45 wherein the metal oxide catalyst comprises at least one Group IIA metal oxide.

54. The process of claim 45 wherein the metal oxide catalyst comprises a Group IIA metal oxide and a Group IIIA metal oxide.

55. The process of claim 45 wherein the metal oxide catalyst comprises a Group IIA metal oxide and a Group IIIB metal oxide.

56. The process of claim 45 wherein the metal oxide catalyst comprises magnesium oxide and aluminum oxide.

57. The process of claim 45 wherein the metal oxide catalyst comprises a mixed metal oxide.

58. The process of claim 45 wherein the ether comprises a substituted or unsubstituted ether.

59. The process of claim 45 wherein the ether comprises monoethylene glycol dimethyl or diethyl ether, diethylene glycol dimethyl or diethyl ether, triethylene glycol dimethyl or diethyl ether, tetraethylene glycol dimethyl or diethyl ether, a polyethylene glycol dimethyl or diethyl ether, bisglycidyl ether, a polyethylene glycol diisopropyl ether, a polyethylene glycol dibutyl ether or a polyethylene glycol diallyl ether.

60. The process of claim 1 wherein said decarboxylation is carried out at a temperature from about 150° C. to about 500° C.

61. The process of claim 28 wherein said transesterification is carried out at a temperature from about ambient to about 300° C.

62. The process of claim 28 wherein said decarboxylation is carried out at a temperature from about 150° C. to about 500° C.

63. The process of claim 45 wherein said decarboxylation is carried out at a temperature from about 150° C. to about 500° C.

64. The process of claim 29 wherein the active hydrogen-containing compound comprises an alcohol having about two to six hydroxyl groups.

65. The process of claim 46 wherein the active hydrogen-containing compound comprises an alcohol having about two to six hydroxyl groups.

* * * * *